United States Patent [19]
Freitas

[11] Patent Number: 5,312,373
[45] Date of Patent: May 17, 1994

[54] SURGICAL ENDOSCOPIC CANNULA WITH POSITIVE TOUCH

[75] Inventor: Michael W. Freitas, Irving, Tex.

[73] Assignee: Dexide, Inc., Fort Worth, Tex.

[21] Appl. No.: 821,085

[22] Filed: Jan. 16, 1992

Related U.S. Application Data

[63] Continuation-in-part of Ser. No. 656,951, Feb. 19, 1991, Pat. No. 5,125,910.

[51] Int. Cl.⁵ .................................. A61M 5/00
[52] U.S. Cl. .................................... 604/249
[58] Field of Search ............... 604/173, 246, 249, 169, 604/167, 164, 158, 264, 902, 33, 30, 35

[56] References Cited

U.S. PATENT DOCUMENTS

| | | | |
|---|---|---|---|
| 4,456,223 | 6/1984 | Ebling | 604/33 X |
| 4,655,752 | 4/1987 | Honkanen et al. | 604/167 X |
| 4,696,305 | 9/1987 | von Berg | 604/249 X |
| 4,776,840 | 10/1988 | Freitas et al. | 604/35 X |

Primary Examiner—Gene Mancene
Assistant Examiner—Jeffrey A. Smith

[57] ABSTRACT

A positive touch surgical endoscopic cannula assembly in which one, or both, of liquid or gas may be introduced or removed from a body cavity during surgery. The device contains a valving mechanism responsive to finger or thumb touch of the surgeon and having a conically shaped force resistor which is partially inverted during movement of the valve between open and closed positions. The partial inversion of the flexible resistor is detectable through an actuator to the hand or thumb of the operator to positively indicate positioning of the valve head and seat members.

7 Claims, 4 Drawing Sheets

SURGICAL ENDOSCOPIC CANNULA WITH POSITIVE TOUCH

CROSS REFERENCE TO RELATED APPLICATION

This application is a continuation-in-part application of co-pending application Ser. No. 656,951, filed Feb. 19, 1991, now U.S. Pat. No. 5,125,910, entitled "Surgical Endoscopic Suction/Irrigation Cannula Assembly", and assigned to the same assignee as the present application.

BACKGROUND OF THE INVENTION (1) Field of the Invention

The invention relates to a surgical endoscopic suction/irrigation cannula assembly including a valve actuator.

(2) Brief Description of the Prior Art

Surgical endoscopic procedures typically follow three steps. First, a cannula, such as a Veress cannula, is inserted into the abdominal cavity through the abdominal wall and the cavity is inflated with insufflating gas which is passed through the cannula tubular housing. After insufflation, a small incision is made in the skin and a standard trocar spike is thrust into the inflated abdomen through the bore of the trocar tube. The spike is inserted for purposes of puncturing or cutting of the abdominal wall and piercing the fascio and peritoneum inside the cavity. After removal of the spike, a suction-/irrigation cannula is inserted through the trocar housing and into the opening so that fluids may be drained from the body cavity.

Endoscopic surgery also includes the introduction through a trocar tube of a number of auxiliary surgical instruments such as, for example, a laparoscope, or the like. Heretofore, in many surgical instances, endoscopic surgery procedures have been performed through the trocar tubular housing by sequential insertion and removal of surgical instruments as they are needed. As the surgery is performed using such instruments, many situations require concurrent introduction or removal of gaseous or liquid fluid materials immediate the area of the surgery. Thus, removal of the surgical instrument from the body cavity through the trocar tubular housing and reinsertion through the trocar housing of a device for transmission of the gaseous or liquid substance not only complicates the surgical procedure, but is also time consuming and may introduce unforeseeable consequences to the surgical operation.

Endoscopic surgery is a very fine art, demanding extremely controlled movements of the surgeon's hand in the operation of the surgical instruments through the trocar housing. Therefore, any valves or other components which are required to be manually manipulated by the surgeon must be extremely sensitive and manipulatable in direct response to a very minor application of pressure or movement of the surgeon's hand or finger.

In copending application Ser. No. 656,951, filed Feb. 19, 1991, now U.S. Pat. No. 5,125,910, and entitled "Surgical Endoscopic Suction/Irrigation Cannula Assembly", and assigned to the same assignee as the present invention, there is shown and disclosed a "trumpet'-'—like valve assembly and cannula for use in irrigation/suction techniques for endoscopic surgery. The present invention is provided in order to enhance the sensitivity of such a device to hand manipulation by the surgeon and to afford the surgeon a positive "feel", indicative of the movement of the valve to the open position. Accordingly, the invention permits the introduction or removal of fluid to or from the body cavity during surgery by activation with only a minor amount of pressure through the surgeon's finger and provides a positive indication, transmittable through the device and the operating finger of the surgeon, indicative of the positioning of the valve head to open a fluid flow passageway.

The present invention also provides for introduction or removal of fluid from the body cavity during surgery through the cannula housing through which an auxiliary device may be inserted at any time during the surgery without removal of the valve actuator device. Thus, an auxiliary endoscopic instrument may be utilized concurrently with the device of the present invention to introduce and/or remove gaseous or liquid fluids from the body cavity during the surgical operation.

SUMMARY OF THE INVENTION

The present invention provides a positive touch surgical endoscopic cannula assembly, as well as a valve actuator assembly for incorporation onto an endoscopic surgical instrument in which gas or liquid is to be introduced and/or removed from a body cavity during surgery. An elongate tubular housing has a first open end for introduction into the body cavity during surgery, and an opposite second open end. A valve actuator assembly is carried on the tubular housing through the second open end with the valve actuator assembly including an actuator housing. At least one valve chamber is provided within the actuator housing. A valve head member is movable between first and second positions and housed within the chamber. A valve seat is defined in the chamber for selective sealing receipt of the valve head when the valve head is in the first position. Biasing means, such as a spring, are provided within the chamber for urging the valve head toward the first position. A manually operable valve head controller is carried on the housing for overcoming the bias of the biasing means and moving the valve head toward the second position. A conically shaped flexible force resistor means has a normal non-inverted state as well as an inverted state and is spaced in the chamber between the housing and the head controller. The resistor means resists movement of the controller in one direction when in the normal state and is at least partially invertible in response to movement of the valve head controller and movement of the valve head toward the second position, whereby movement of the resistor to the partially inverted state will terminate resistance upon movement of the valve head controller. A fluid passageway is included in the chamber and extends within the actuator housing and through the elongate tubular housing. A port is disposed through the actuator housing and is in fluid communication with the chamber for receiving a fluid transmitting means for directing fluid into or out of the tubular housing through the chamber.

In an alternate preferred embodiment, an assembly is provided in which ports are disposed through the lower most portion of the actuator housing which are, in turn, in fluid communication with a fluid chamber upstream of a valve head which is normally biased toward its sealing valve seat. In such configuration, the valve will always remain closed regardless of the exposure of the device to increased pressures. In other words, the more pressure which is received through the ports, the more

3 the valve heads are urged into sealing engagement with the valve seat.

DESCRIPTION OF THE PREFERRED EMBODIMENTS

Figure 1:
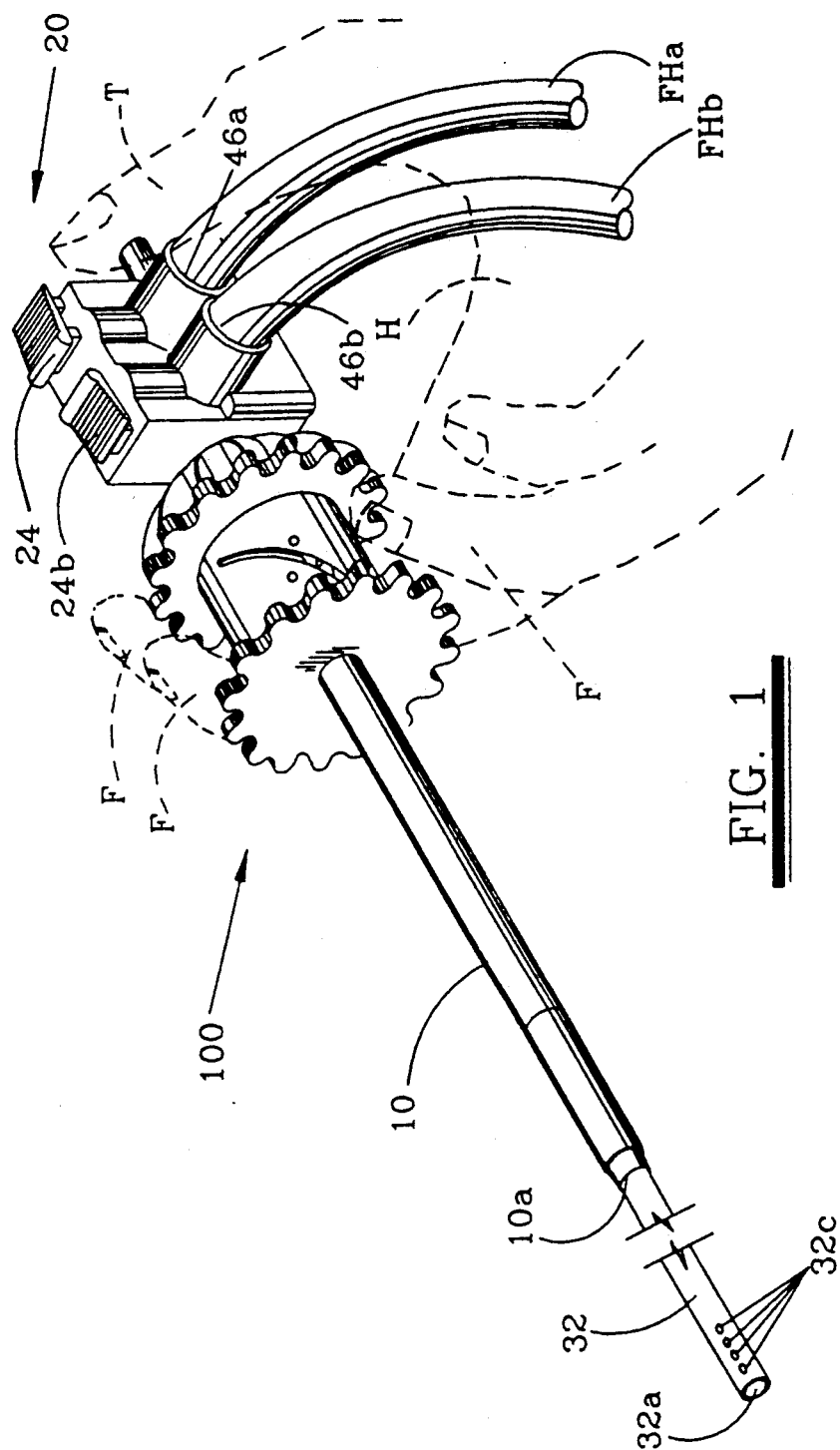
FIG. 1 is an isometric view of the surgical endoscopic cannula assembly introduced through a trocar housing and held in the hands of a surgical operator.

Now, with first reference to FIG. 1, there is shown the surgical endoscopic cannula assembly 100 of the present invention disposed through an elongate tubular cannula housing 10 and held in such position prior to use during surgery and introduction through a body cavity by means of application of a surgeon's fingers F while the surgeon's thumb T on hand H grasps the end of a valve actuator assembly 20.

An elongate tubular housing 32 of the actuator assembly 20 is shown extending through the outboard-most open end 10a of the cannula housing 10, with the elongate tubular housing 32 having a first open end 32a with transverse ports 32c intermediate the open end 32a.

As shown in FIG. 1, plural fluid hoses FHa, FHb are secured to the valve actuator assembly 20 through respective ports 46a, 46b, with the hoses FHa, FHb, extending to a body of pressured fluid for introduction through the actuator assembly 20 and the housing 32 and into the body cavity during surgery, and/or to a vacuum generating means for removal of fluid, by suction, through the open end 32a, thence through the housing 32 and into the actuator assembly 20, during the surgical operation.

Figure 2:
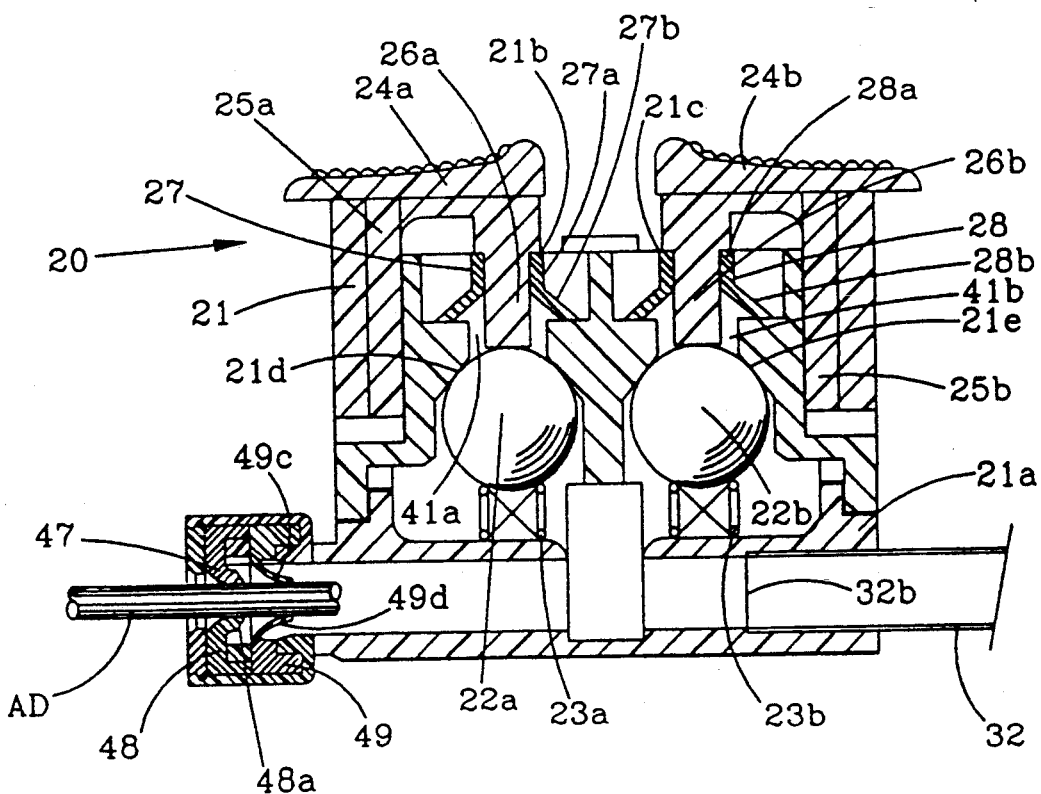
FIG. 2 is a partial sectional view through the valve actuator assembly with the valve members therein being in closed position.

Now referring to FIG. 2, there is shown the valve actuator assembly 20 of the present invention with plural valve assemblies therein. The actuator is defined by an exterior actuator housing 21 having a lower body member 21a for sealing receipt of the second open end 32b of the elongate tubular housing 32.

With continued reference to FIG. 2, the valve actuator assembly 20 includes within the housing 21 first and second valve head spherical members 22a, 22b, which are biased by means of respective springs 23a, 23b, toward a companionably contoured valve seat portion 21d, 21e on the housing 21.

A finger or thumb activated controller 24a, 24b is provided for each of the valve heads 22a, 23b. The controllers 24a, 24b have respective extensions 25a, 25b extending within the housing 21 and inner extending end 26a, 26b extending within a passage 21b, 21c through the top of the housing 21. The ends 26a, 26b extend to the outer surface of the respective valve head 22a, 22b.

Extending around the exterior of the respective end elements 26a, 26b and within the housing 21 are first and second force resistors 27 and 28. The force resistors are of an elastomeric rubber-like material and are normally conically shaped, each having an upper cone portion 27a, 28a extending to a lower outwardly extending conical skirt portion 27b, 28b, with the lower end of the respective skirt portions 27b, 28b being carried on the housing 21 at the uppermost end of the valve seat portion 21d, 21e above the respective valve heads 22a, 22b.

Valve chambers 41a, 41b, are defined exteriorally around the respective valve head members 22a, 22b, interior of the actuator housing 21, and are always in communication through respective ports 46a, 46b with the respective fluid hose FHa, FHb.

Figure 3:
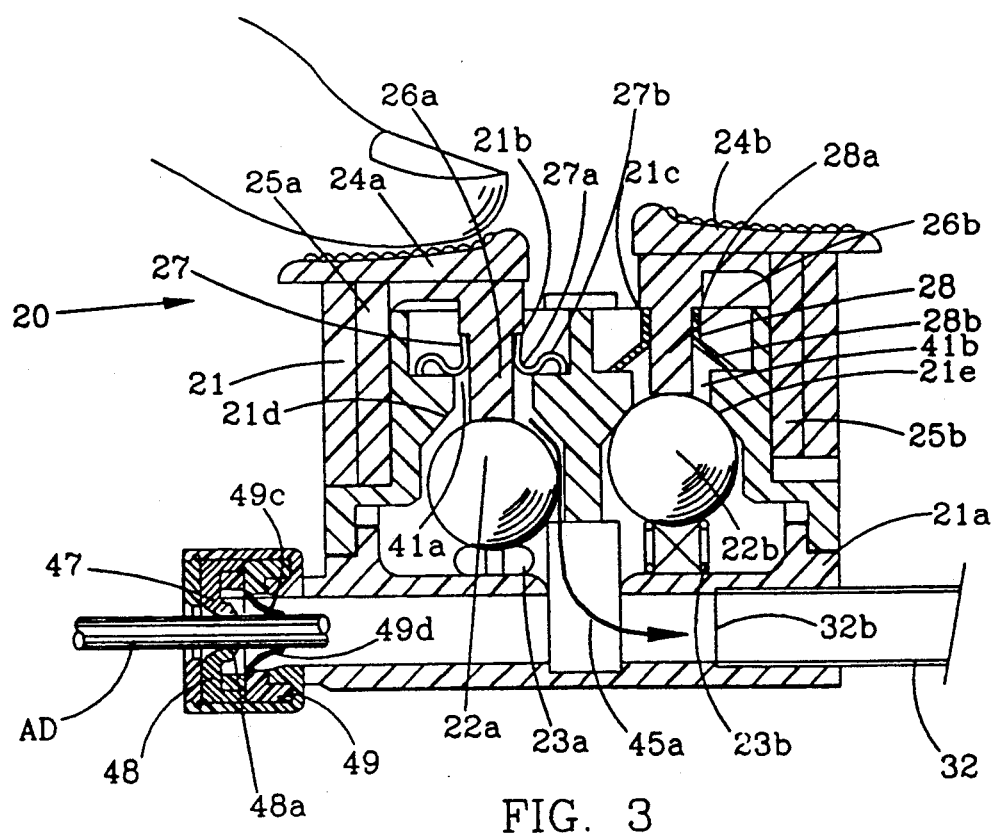
FIG. 3 is a view similar to that of FIG. 2 showing one of the valve members in the actuator being opened for passage of fluid therethrough.
Figure 4:
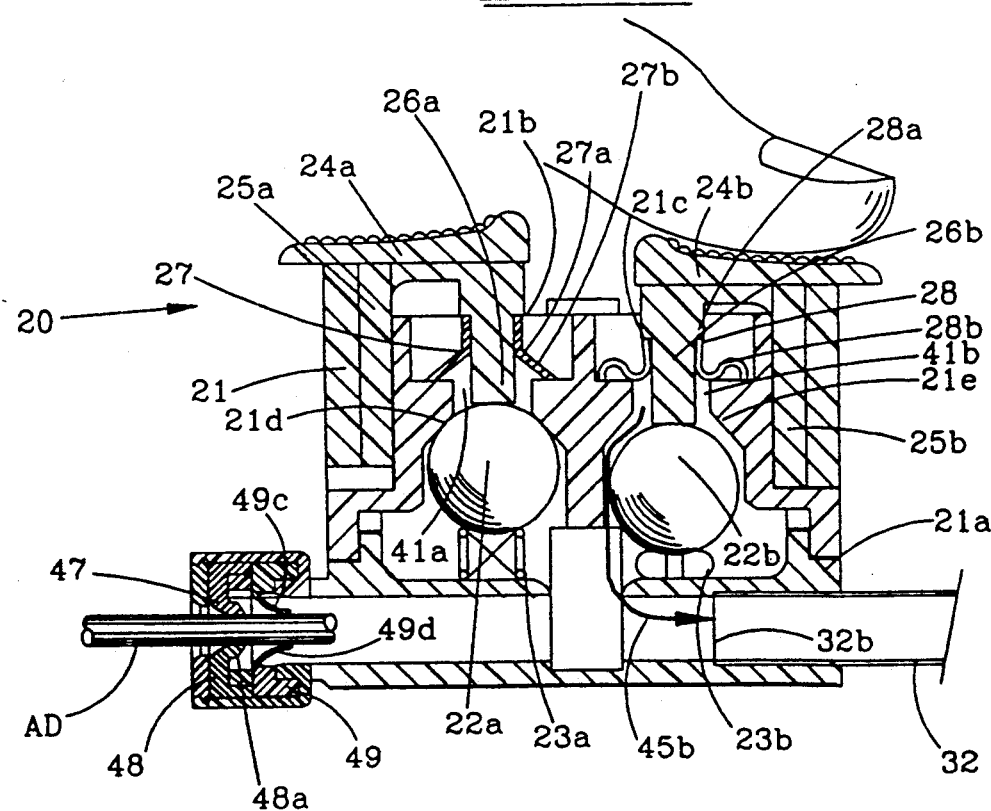
FIG. 4 is a view similar to that of FIGS. 2 and 3, showing the other of the valve members in the actuator being opened and the first valve member being closed for transmission of another fluid therethrough.

Fluid passageways 45a (FIG. 3) is defined in the actuator assembly 20 and includes the valve chamber 41a when the valve seat 21d is sealingly away from its valve head 22a (FIG. 2). Likewise, a fluid passageway 45b (FIG. 4) extends from the fluid hose FHb by means of the port 46b through the chamber 41b when the valve head 23b is sealingly away from its valve seat 21e (FIG. 4). These fluid passageways 45a, 45b, may carry fluid in a form of a liquid in one or both of the fluid hoses FHa, FHb, for introduction into the actuator assembly 20 and the tubular cannula housing 10, and discharged through the open end 32a and the transverse ports 32c into the body cavity during surgery. Alternatively, one or both of the fluid passageways 45a, 45b, may provide a fluid vacuum passage extending to one or both of the fluid hoses FHa, FHb, for removal of fluid from the body cavity during surgery.

The actuator housing 21 also has a selectively openable port 47 opposite the opening in housing member 21a for receipt of the member 32, for introduction of an auxiliary device AD, such as a laparoscope, which may be concurrently utilized during the surgery in combination with the actuator assembly 20. As will be appreciated from the disclosure herein, and, particularly with respect to FIGS. 1 and 2, the auxiliary device AD may be introduced through the valve actuator assembly 20 and the elongate tubular cannula housing 10 and the tubular housing 32 of the assembly 100 while concurrently manipulating one or both of the valve head controllers 24a, 24b, to introduce or remove fluid during surgery.

The port 47 is always sealingly closed by means of a seal assembly comprising a first seal 48 and a second seal means 49. The first seal 48 has a concave curvature 48a and incorporates a lateral slit to accommodate entrance of the auxiliary device AD therethrough. When the auxiliary device AD is introduced through the assembly 20, as shown in FIGS. 2, 3 and 4, first and second seal means 49c and 49d will seal around the exterior of auxiliary device AD to prevent passage of fluid and pressure there across from the interior of the assembly 20, to the exterior thereof, through the port 47. Additionally, when the auxiliary device AD is not within the assembly 20, the seal means 48 prevents fluids from passing from the exterior to the interior, and vice versa.

OPERATION

When it is desired to perform endoscopic surgery, the cannula housing 10 is introduced through the body cavity and held by the surgeon, as shown in FIG. 1. The valve actuator assembly 20 may be introduced into the cannula housing 10 prior to introduction of housing 10 into the body cavity, or concurrently therewith, or subsequent thereto.

When it is desired to introduce or remove fluid to or from the body cavity, one or more of the valve head controllers 24a, 24b are manipulated to move the respective valve heads 22a, 22b, from sealing engagement with the respective valve seat 21d, 21e, by placing the thumb T or finger F of the hand H of the surgeon on the respective controller 24a and applying a downward slight force thereon and toward the interior of the housing 21. Accordingly, as force is applied through the controller 24a in such fashion, the end 26a will engage the valve head 22a to begin movement away from the valve seat 21d and sealing engagement relative thereto. Concurrently, the bias of the spring 23a will be overcome and the spring 23a will begin to compress.

Because of the elasticity and snug engagement of the force resistor 27 around the exterior of the end portion 26a, slight resistance to movement of the controller 24a by the thumb T or finger F will occur. As the controller 24a continues to be moved, the load on the flexible elastomeric force resistor 27 will cause a slight "inversion" of the conical shape thereof between the upper cone portion 27a and the conical skirt 27b such that the resistor 27 configuration inverts from the form shown in FIG. 2 to that in FIG. 3 (for controller 24a) or FIG. 4 (for controller 24b). When the "inversion" of the force resistor 27 is effected, load through the end 26a of the controller 24a will be immediately directly transferred to the valve head 22a without resistance and such immediate transfer can be felt through the thumb T or finger F of the surgeon through the controller 24a by a slight "snap" thrust movement through the controller 24a. Such an indication is reflective of the valve head 22a being moved to the open position.

The same sequential operation will be produced when the controller 24b is manipulated.

The auxiliary device AD may be inserted through the apparatus 100 either prior to subsequent to activation of the controller 24a, 24b, as described above.

Figure 5:
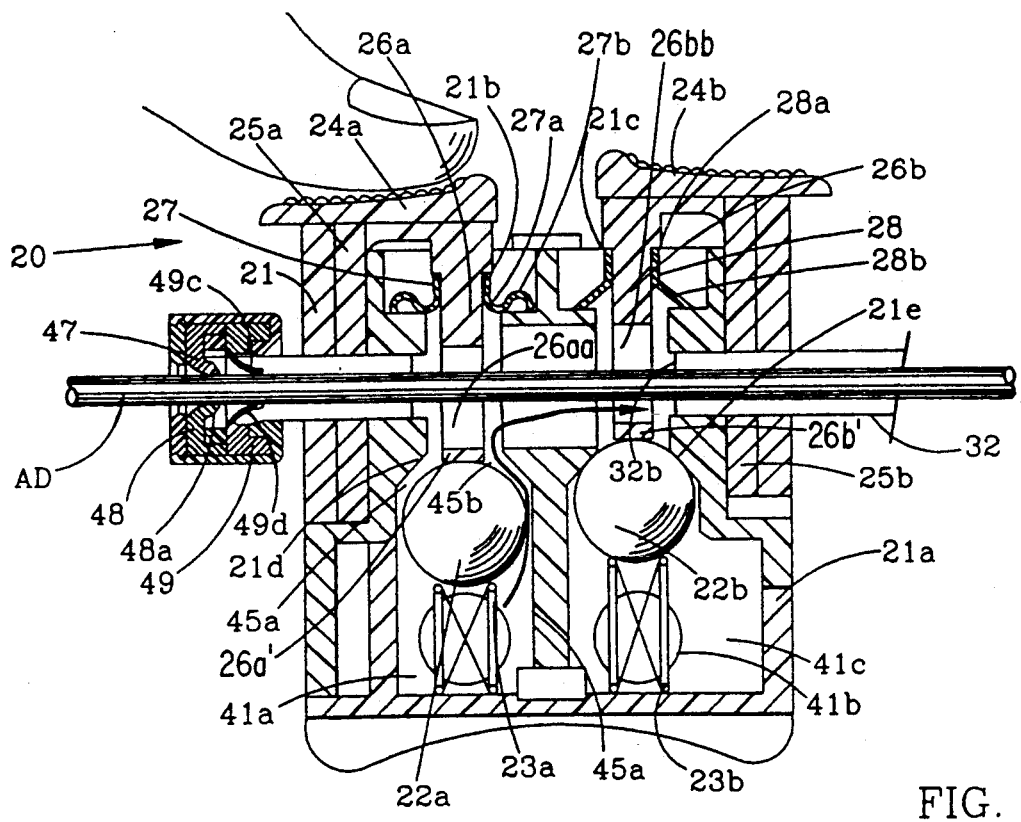
FIG. 5 is a view similar to that of FIG. 3, but illustrating the alternate preferred embodiment of the present invention.
Figure 6:
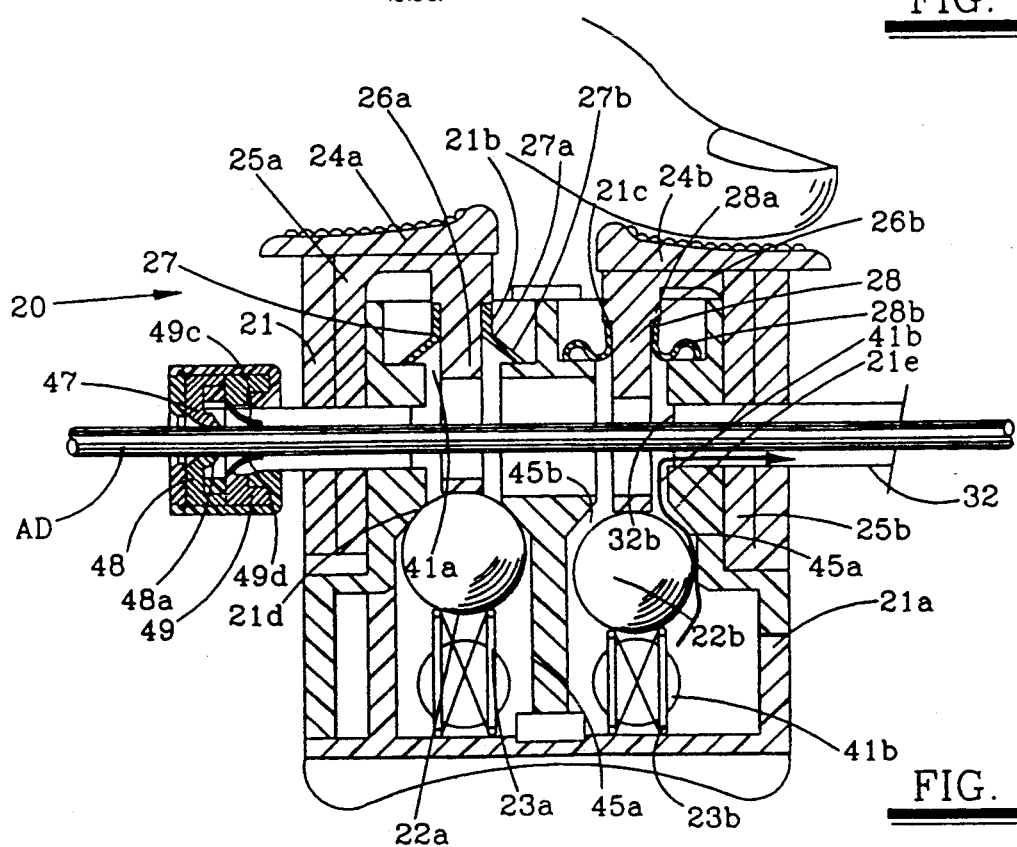
FIG. 6 is a view similar to that of FIG. 4, illustrating the alternate preferred embodiment with the other of the valve members in the actuator being opened and the first valve member being closed for transmission of another fluid therethrough.

Now with reference to FIGS. 5 and 6, there is shown an alternate preferred embodiment of the assembly 20, wherein like numbers are used for like parts. In such alternate preferred embodiment, it will be appreciated that the ports 46a, 46b are placed within the lower body member 21a and upstream of the respective spherical valve head members 22a, 22b, with the respective biasing means, or springs, 23a, 23b, also being placed upstream of the spherical members 22a, 22b. Additionally, the elongate tubular housing 32 is positioned through the assembly 20 and within the housing 21 and are downstream of the respective spherical valve heads 22a, 22b. Each of the inner ends 26a, 26b, extending from the controller 24a, 24b, is provided with a passageway 26aa 26bb which, when the valve heads 22a, 22b, are in sealing engagement on the valve seats 21d, 21e, provides full opening relative to the inner diameter of the elongate tubular housing member 32, such that auxiliary devices may be inserted therethrough. Each of the inner ends 26a, 26b of the respective controllers 24a, 24b have a solid tip end 26a', 26b' which contacts the upper surface of the respective valve head spherical member 22a, 22b, such that when the respective controller 24a, 24b is manipulated by the operator, the respective tip end 26a', 26b' will contact the outer upper surface of the respective valve heads spherical element 22a, 22b, to overcome the bias of the spring 23a, 23b, as well as the pressure within the chamber 41a, 41b through the port 46a, 46b, to manipulate the spherical 22a, 22b, away from the respective seat 21d, 21e, to open the fluid flow passageway between the chamber 41a, 41b, and the elongate tubular housing 32.

It will be appreciated that the inner diameter of the respective passageways 26aa, 26bb, through the inner ends 26a, 26b, is slightly larger than the inner diameter of the elongate tubular housing member 32 in order to provide full opening clearance through the members 26a, 26b, while the spherical members 22a, 22b, in the assembly 20 are manipulated from closed to opened position to permit fluid communication thereacross while having an auxiliary instrument housed within the assembly 20 and the elongate tubular housing 32. Thus, in the alternative preferred embodiment of the apparatus shown in FIGS. 5 and 6, the ports 46a and 46b are on the same side of the ball valve heads 22a, 22b as is the biasing means 23a, 23b, in other words, when the fluid passing through the lines FHa, FHb, and into the respective ports 46a and 46b is to be an irrigating liquid, the ports 46a, 46b and the biasing means 23a, 23b will be upstream with respect to the valve head members 22a, 22b, with respect to the direction of flow of fluid within the actuator 20. Likewise, the second opened end 32b of the elongate tubular housing 32 is "downstream" of the area of sealing engagement between the respective valve heads 22a, 22b, and the valve seats 21d, 21e.

Although the invention has been described in terms as specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A positive touch surgical endoscopic cannula assembly comprising:

an elongate tubular housing having a first open end for introduction into a body cavity during surgery, and a second open end;

a valve actuator assembly carried on said tubular housing through said second open end, said valve actuator assembly including an actuator housing;

at least one valve chamber within said actuator housing;

a spherical valve head member moveable between first and second positions housed within said at least one valve chamber;

a valve seat defined in said at least one valve chamber for selective sealing receipt of said valve head in said first position;

biasing means in said chamber for urging said valve head toward said first position;

a manually operable valve head controller carried on said actuator housing for overcoming the bias of said biasing means and moving the valve head toward said second position;

a conically shaped flexible force resistor means having a normal non-inverted state and a partially inverted state, and being spaced in said at least one valve chamber between said housing and said valve head controller, said resistor means resisting movement of said controller in one direction when in said normal state, and being at least partially inverted in the response to movement of said valve head controller and movement of said valve head toward said second position, whereby movement of said resistor to said partially inverted state terminates resistance upon movement of said valve head controller;

a fluid passageway including said at least one valve chamber and extending within said actuator housing and through said elongate tubular housing;

and a port disposed through said actuator housing and in fluid communication with said at least one chamber for receiving a fluid transmitting means for directing fluid into or out of said tubular housing through said chamber.

2. The cannula assembly of claim 1, wherein said port is upstream of said valve head and said biasing means.

3. The cannula assembly of claim 2, wherein said second open end of said elongate tubular housing is downstream of said valve head and valve seat.

4. A positive touch surgical endoscopic cannula assembly, comprising:

an elongate tubular housing having a first open end for introduction into a body cavity during surgery, and a second open end;

a valve actuator assembly carried on said tubular housing through said second open end, said valve actuator assembly including an actuator housing;

at least one valve chamber within said actuator housing;

a valve head member moveable between first and second positions housed within said at least one valve chamber;

a valve seat defined in said at least one valve chamber for selective sealing receipt of said valve head in said first position;

biasing means in said at least one valve chamber for urging said valve head toward said first position;

a manually operable valve head controller carried on said actuator housing for overcoming the bias of said biasing means and moving the valve head toward said second position;

a conically shaped flexible force resistor means having a normal non-inverted state and a partially inverted state, and being spaced in said at least one valve chamber between said housing and said vale head controller, said resistor means resisting movement of said controller in one direction when in said normal state, and being at least partially inverted in the response to movement of said valve head controller and movement of said valve head toward said second position, whereby movement of said resistor to said partially inverted state terminates resistance upon movement of said valve head controller;

a fluid passageway including said at least one valve chamber and extending within said actuator housing and through said elongate tubular housing;

and a port disposed through said actuator housing and in fluid communication with said at least one valve chamber for receiving a fluid transmitting means for directing fluid into or out of said tubular housing through said at least one valve chamber, said port being upstream of said valve head and said biasing means, said second opened end of said elongate tubular housing being down-stream of said valve head and valve seat;

and wherein said valve head controller includes a passageway disposed therethrough for insertion of an auxiliary device through said actuator assembly and said elongate tubular housing when said valve head is in each of said first and second positions.

5. A positive touch endoscopic surgical valve actuator assembly for control of fluids selectively transmitted into and out of a body upon which surgery is performed, comprising:

an actuator housing;

at least one valve chamber within said actuator housing;

a spherical valve head member moveable between first and second positions and housed within said at least one valve chamber;

a valve seat defined in said at least one chamber for selective sealing receipt of said valve head when said valve head is in said first position;

biasing means in said chamber for urging said valve head toward said first position;

a manually operable valve head controller carried on said housing for overcoming the bias of said biasing means and moving the valve head toward said second position;

a conically shaped flexible force resistor means having a normal non-inverted state and a partially inverted state and being space in said at least one chamber between said housing and said head controller;

said resistor means resisting movement of said controller in one direction in said normal state and being at least partially inverted in response to movement of said valve head controller and movement of said valve head toward said second position, whereby movement of said resistor to said partially inverted state terminates resistance upon movement of said valve head controller.

6. A positive touch surgical endoscopic cannula assembly, comprising:

an elongate tubular housing having a first open end for introduction into a body cavity;

and a second open end;

a valve actuator assembly carried on said tubular housing and in fluid communication with said tubular housing through said second open end, said valve actuator assembly including an actuator housing;

first and second valve chambers within said housing;

a valve head member disposed within each of said valve chambers and moveable between first and second positions;

a valve seat defined in each of said valve chambers for selective sealing receipt of a valve head thereon when said valve head is on said first position;

biasing means in each of said valve chambers for urging said respective valve heads toward said first position;

a manually operable valve head controller carried on said housing and disposable within each of said chambers for overcoming the bias of said biasing means in moving the respective valve heads toward said second position;

conically shaped flexible force resistor means having a normal non-inverted and a partially inverted state, and being spaced in each of said valve chambers between said housing and said head controller, said resistor means resisting movement of said head controller in one direction when in said normal state and being at least partially inverted in response to movement of said respective valve head controller and movement of said respective valve head toward said second position, whereby movement of said resistor to said partially inverted state terminates resistance upon movement of said respective valve head controller;

first and second fluid passageways including said chambers and extending within said tubular housing, one of said passageways being intercepted by one of said valve head and valve seats and other of said fluid passageways being intercepted by the other of said valve head and valve seats, one of said fluid passageways providing means for transmission of liquid therethrough and the other of said fluid passageways providing means for transmission of a gaseous vacuum therethrough;

and first and second ports disposed through said housing and in respective communication with said first and second chambers for receiving a fluid transmitting means for urging fluid into and out of said tubular housing through said respective chambers.

7. A positive touch surgical endoscopic cannula assembly comprising:

an elongate tubular housing having a first open end for introduction into a body cavity during surgery, and a second open end;

a valve actuator assembly carried on said tubular housing through said second open end, said valve actuator assembly including an actuator housing;

at least one valve chamber within said actuator housing;

a valve head member moveable between first and second positions housed within said at least one valve chamber;

a valve seat defined in said at least one valve chamber for selective sealing receipt of said valve head in said first position;

biasing means in said chamber for urging said valve head toward said first position;

a manually operable valve head controller carried on said actuator housing for overcoming the bias of said biasing means and moving the valve head toward said second position;

a conically shaped flexible force resistor means having a normal non-inverted state and a partially inverted state, and being spaced in said at least one valve chamber between said housing and said valve head controller, said resistor means resisting movement of said controller in one direction when in said normal state, and being at least partially inverted in the response to movement of said valve head controller and movement of said valve head toward said second position, whereby movement of said resistor to said partially inverted state terminates resistance upon movement of said valve head controller;

a fluid passageway including said at least one valve chamber and extending within said actuator housing and through said elongate tubular housing;

a port disposed through said actuator housing and in fluid communication with said at least one chamber for receiving a fluid transmitting means for directing fluid into or out of said tubular housing through said chamber;

a selectively openable port disposed through said actuator housing and in alignment with said elongate tubular housing for sealing introduction and removal of an auxiliary device through said assembly and into said body cavity; and means for continuously sealing said selectively openable port to prevent fluid transmission therethrough before, during and subsequent to introduction and removal of said auxiliary device therethrough.

* * * * *